(12) United States Patent
Murakoshi et al.

(10) Patent No.: US 10,709,337 B2
(45) Date of Patent: Jul. 14, 2020

(54) PHOTOACOUSTIC MEASUREMENT APPARATUS AND PHOTOACOUSTIC MEASUREMENT SYSTEM

(71) Applicant: FUJIFILM Corporation, Tokyo (JP)

(72) Inventors: Dai Murakoshi, Ashigarakami-gun (JP); Kaku Irisawa, Ashigarakami-gun (JP); Tetsuro Ebata, Ashigarakami-gun (JP); Shoji Hara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 325 days.

(21) Appl. No.: 15/636,947

(22) Filed: Jun. 29, 2017

(65) Prior Publication Data

US 2017/0296061 A1    Oct. 19, 2017

Related U.S. Application Data

(63) Continuation of application No. PCT/JP2015/084095, filed on Dec. 4, 2015.

(30) Foreign Application Priority Data

Jan. 8, 2015    (JP) ................. 2015-002195

(51) Int. Cl.
*A61B 5/00* (2006.01)
*A61B 8/13* (2006.01)
*A61B 8/08* (2006.01)
*A61B 8/00* (2006.01)

(52) U.S. Cl.
CPC .......... *A61B 5/0095* (2013.01); *A61B 8/085* (2013.01); *A61B 8/13* (2013.01); *A61B 8/461* (2013.01); *A61B 8/5207* (2013.01); *A61B 5/7225* (2013.01)

(58) Field of Classification Search
CPC ..... A61B 5/0095; A61B 5/7225; A61B 8/085; A61B 8/461; A61B 8/5207; G06T 7/0012
See application file for complete search history.

(56) References Cited

U.S. PATENT DOCUMENTS

2012/0203093 A1    8/2012   Imran et al.
2012/0283564 A1*  11/2012   Ebbini ............... A61B 8/06
                                              600/439

(Continued)

FOREIGN PATENT DOCUMENTS

CN           1883379 A       12/2006
JP        2009-506871 A       2/2009

(Continued)

OTHER PUBLICATIONS

Favazza, Christopher P., Lihong V. Wang, and Lynn A. Cornelius. "In vivo functional photoacoustic microscopy of cutaneous microvasculature in human skin." Journal of biomedical optics 16, No. 2 (2011): 026004.*

(Continued)

*Primary Examiner* — Carolyn A Pehlke
(74) *Attorney, Agent, or Firm* — Birch, Stewart, Kolasch & Birch, LLP

(57) ABSTRACT

In a photoacoustic measurement apparatus and a photoacoustic measurement system, blood flow information in a desired region can be generated using a photoacoustic image. A light source emits measurement light. A probe detects a photoacoustic wave generated in a subject after measurement light is emitted to the subject in each of the avascularized condition in which the subject is avascularized and the non-avascularized condition in which the subject is not avascularized. Photoacoustic image generation unit generates a photoacoustic image based on the detection signal of the photoacoustic wave. Blood flow information generation (Continued)

unit generates blood flow information based on the signal value of a photoacoustic image in a region of interest set in the photoacoustic image.

20 Claims, 7 Drawing Sheets

(56) References Cited

U.S. PATENT DOCUMENTS

| | | | |
|---|---|---|---|
| 2012/0330112 A1* | 12/2012 | Lamego | G06F 19/00 |
| | | | 600/301 |
| 2013/0184555 A1 | 7/2013 | Chen et al. | |
| 2016/0260212 A1* | 9/2016 | Ouji | G06T 7/20 |

FOREIGN PATENT DOCUMENTS

| | | |
|---|---|---|
| JP | 2012-113191 A | 6/2012 |
| WO | WO 2009/057019 A1 | 5/2009 |
| WO | WO 2014/207440 A1 | 12/2014 |

OTHER PUBLICATIONS

Harrison, Tyler, Janaka C. Ranasinghesagara, Huihong Lu, Kory Mathewson, Andrew Walsh, and Roger J. Zemp. "Combined photoacoustic and ultrasound biomicroscopy." Optics express 17, No. 24 (2009): 22041-22046.*

Extended European Search Report, dated Nov. 24, 2017, for European Application No. 158769737.

International Preliminary Report on Patentability and English translation of Written Opinion of the International Searching Authority for PCT/JP2015/084095 (Forms PCT/IB/373 and PCT/ISA/237) dated Jul. 11, 2017.

International Search Report (PCT/ISA/210) issued in PCT/JP2015/084095, dated Feb. 9, 2016.

Written Opinion of the International Searching Authority (PCT/ISA/237) issued in PCT/JP2015/084095, dated Feb. 9, 2016.

European Office Action, dated Feb. 5, 2019, for European Application No. 15876973.7.

European Communication pursuant to Article 94(3) EPC for European Application No. 15876973.7, dated Aug. 8, 2019.

* cited by examiner

PHOTOACOUSTIC MEASUREMENT APPARATUS AND PHOTOACOUSTIC MEASUREMENT SYSTEM

CROSS-REFERENCE TO RELATED APPLICATIONS

This application is a Continuation of PCT International Application No. PCT/JP2015/084095 filed on Dec. 4, 2015, which claims priority under 35 U.S.C. § 119(a) to Japanese Patent Application No. 2015-002195 filed on Jan. 8, 2015. Each of the above application(s) is hereby expressly incorporated by reference, in its entirety, into the present application.

BACKGROUND OF THE INVENTION

1. Field of the Invention

The present invention relates to a photoacoustic measurement apparatus and a photoacoustic measurement system, and more particularly, to a photoacoustic measurement apparatus and a photoacoustic measurement system for detecting photoacoustic waves generated in a subject after emitting light to the subject.

2. Description of the Related Art

As a prior art that restricts a blood flow from the outside and releases the restriction to evaluate the perfusion state of the blood flow, a skin perfusion pressure (SPP) measuring apparatus is known (for example, JP2009-506871A). The SPP measuring apparatus emits laser light to a measurement part. The amount and the Doppler shift of reflected light with respect to the emitted laser light change according to a blood flow. The amount and the Doppler shift of reflected light are measured while changing the cuff pressure from high pressure to low pressure, a cuff pressure at which the blood flow abruptly increases is calculated, and the cuff pressure is displayed as "skin perfusion pressure".

For the observation of the blood flow, JP2012-113191A discloses a method of generating a blood flow image. In JP2012-113191A, a blood flow image is generated by capturing a reflection type confocal laser microscope image of the skin as a motion picture, generating a plurality of brightness difference images between frames of the motion picture, and adding the plurality of brightness difference images. JP2012-113191A discloses temporarily stopping (ischemia) the skin blood flow of the forearm (measurement part), which is distal when viewed from the heart, by wrapping a cuff around the subject's upper arm and pressing it and then releasing the pressure to return to the skin blood flow (reperfusion). JP2012-113191A discloses generating a blood flow image before ischemia, during ischemia, and immediately after reperfusion.

SUMMARY OF THE INVENTION

In JP2009-506871A, since the blood flow is measured at one measurement point, it is not possible to evaluate the spatial distribution of perfusion. In particular, it is not possible to perform evaluation in a depth direction. In JP2012-113191A, it is possible to evaluate the spatial distribution of perfusion with a blood flow image. In JP2012-113191A, however, since observation is performed using a reflection type confocal laser microscope, only the vicinity of the skin surface can be mainly observed.

Here, as a kind of image examination method capable of examining the state of the inside of a living body from the skin surface to a deeper place in a non-invasive manner, photoacoustic imaging for imaging the inside of the living body by using the photoacoustic effect is known. In general, in photoacoustic imaging, pulsed laser light, such as a laser pulse, is emitted into the living body. In the living body, a living tissue absorbs the energy of the pulsed laser light, and ultrasound waves (photoacoustic waves) are generated when adiabatic expansion immediately occurs. By detecting the photoacoustic waves using an ultrasound probe or the like and generating a photoacoustic image based on the detection signal, it is possible to visualize the inside of the living body based on the photoacoustic waves.

The inventors have considered evaluating the perfusion of blood using the photoacoustic image described above. By using short pulse laser light having a wavelength at which absorption in blood is stronger than that in surrounding tissues, such as muscle or fat, as measurement light, it is possible to detect and image the signal of blood (hemoglobin) by detecting photoacoustic waves generated by absorption using a probe. By using a photoacoustic image, it is possible to draw fine blood vessels that are difficult to draw particularly in ultrasound Doppler. In a photoacoustic image, however, stronger photoacoustic waves are generated from the superficial portion. Accordingly, it is thought that it is difficult to evaluate perfusion in a region where a deep portion, capillaries, or the like is present just by simply displaying the photoacoustic image.

In view of the above circumstances, it is an object of the present invention to provide a photoacoustic measurement apparatus and a photoacoustic measurement system capable of generating blood flow information in a desired region using a photoacoustic image.

In order to achieve the aforementioned object, the present invention provides a photoacoustic measurement apparatus comprising: a receiving circuit that receives a detection signal of a photoacoustic wave, which is generated in a subject due to emission of measurement light to the subject, in each of at least an avascularized condition in which the subject is avascularized and a non-avascularized condition in which the subject is not avascularized; a photoacoustic image generation unit for generating a photoacoustic image based on the detection signal of the photoacoustic wave; and a blood flow information generation unit for generating blood flow information based on a signal intensity of the photoacoustic image in a region of interest set in the photoacoustic image.

It is preferable that the photoacoustic measurement apparatus of the present invention further comprises a tourniquet capable of changing a cuff pressure in order to bring the subject into the avascularized condition and the non-avascularized condition.

In the photoacoustic measurement apparatus described above, it is preferable to further comprise a cuff pressure control unit for controlling a cuff pressure of the tourniquet.

The blood flow information generation unit may binarize the signal value by setting the signal value to a first value when the signal value is equal to or greater than a first threshold value and equal to or less than a second threshold value larger than the first threshold value and setting the signal value to a second value different from the first value when the signal value is less than the first threshold value or greater than the second threshold value, and generate the blood flow information based on the binarized signal value.

The blood flow information generation unit may further generate a graph showing a relationship between the blood flow information and time.

It is preferable that the receiving circuit further receives a detection signal of a reflected acoustic wave with respect to an acoustic wave transmitted to the subject. It is preferable that the photoacoustic measurement apparatus further has a reflected acoustic wave image generation unit for generating a reflected acoustic wave image based on the detection signal of the reflected acoustic wave and a region-of-interest tracking unit for tracking a position of the region of interest using the reflected acoustic wave image.

The blood flow information generation unit may generate, as blood flow information, a total value or an average value of the signal value in the region of interest.

The photoacoustic measurement apparatus of the present invention may further comprise a pressure measurement unit for measuring an avascularization pressure of the subject. In this case, the blood flow information generation unit may further generate a graph showing a relationship between the blood flow information and the avascularization pressure.

The blood flow information generation unit may calculate a total value or an average value of the signal value in the region of interest, and generate, as the blood flow information, a score value based on a difference between a minimum value and a maximum value of the total value or the average value in a certain period.

The blood flow information generation unit may generate, as the blood flow information, a score value based on a difference between a total value or an average value of the signal value in the region of interest in the avascularized condition and a total value or an average value of the signal value in the region of interest in the non-avascularized condition.

In a case where the subject is changed from the avascularized condition to the non-avascularized condition, the blood flow information generation unit may generate, as the blood flow information, a score value based on a time change rate of a total value or an average value of the signal value in the region of interest.

In a case where the subject is changed from the avascularized condition to the non-avascularized condition, the blood flow information generation unit may generate, as the blood flow information, a score value based on a total value or an average value of the signal value in the region of interest after a certain time has passed from a reference time.

In a case where the subject is changed from the avascularized condition to the non-avascularized condition, the blood flow information generation unit may generate, as the blood flow information, a score value based on a time from a reference time to a time at which a total value or an average value of the signal value in the region of interest reaches a certain level.

The blood flow information generation unit may further generate a blood flow information image based on the blood flow information.

In a case where a plurality of the regions of interest are set, the blood flow information may be generated for each of the plurality of regions of interest, and the blood flow information image may be a space map image for displaying blood flow information of each region of interest in the region of interest.

In the blood flow information image, it is preferable that each region of interest is displayed with a brightness corresponding to the blood flow information.

The blood flow information generation unit may set a display color of each region of interest in the blood flow information image to a different display color in a case where blood flow information at a first time is larger than blood flow information at a second time earlier than the first time and a case where the blood flow information at the first time is smaller than the blood flow information at the second time.

A plurality of the regions of interest may be set in a grid form.

In addition, the present invention provides a photoacoustic measurement system comprising: a light source that emits measurement light; an acoustic wave detection unit for detecting a photoacoustic wave, which is generated in a subject due to emission of the measurement light to the subject, in each of at least an avascularized condition in which the subject is avascularized and a non-avascularized condition in which the subject is not avascularized; a photoacoustic image generation unit for generating a photoacoustic image based on a detection signal of the photoacoustic wave; and a blood flow information generation unit for generating blood flow information based on a signal value of the photoacoustic image in a region of interest set in the photoacoustic image.

The photoacoustic measurement apparatus and the photoacoustic measurement system of the present invention can generate blood flow information in a desired region using a photoacoustic image.

DESCRIPTION OF THE PREFERRED EMBODIMENTS

Figure 1:
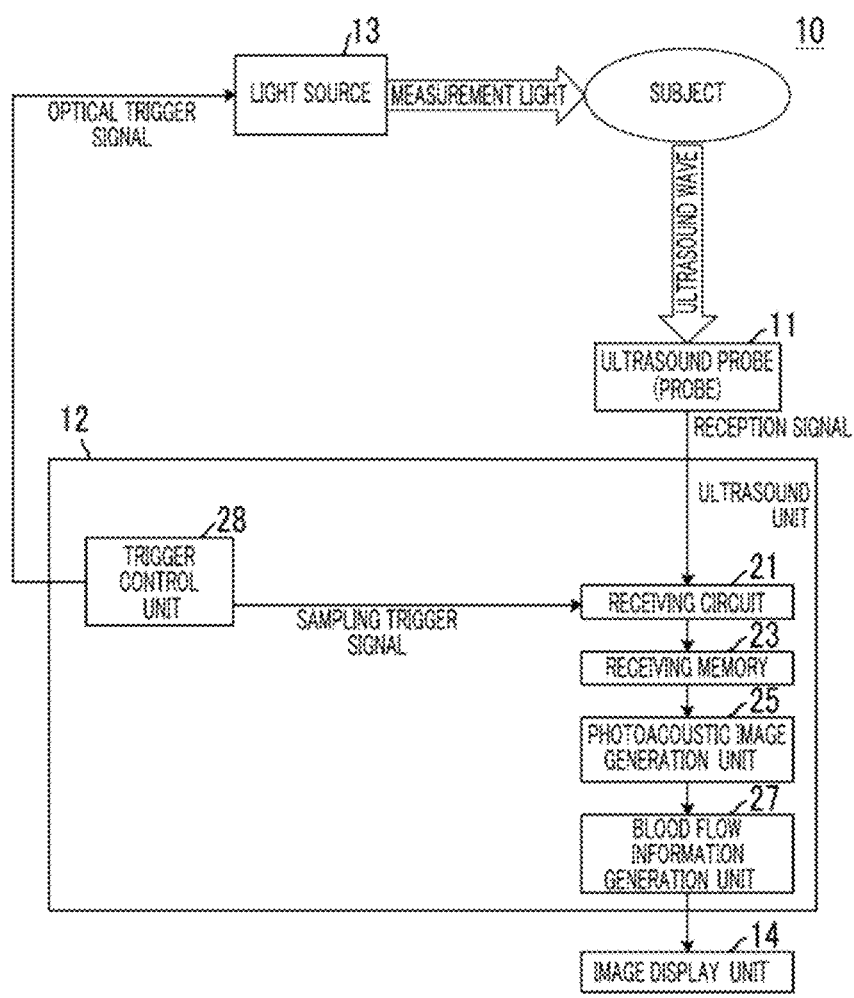
FIG. 1 is a block diagram showing a photoacoustic measurement system including a photoacoustic measurement apparatus according to a first embodiment of the present invention.

Hereinafter, embodiments of the present invention will be described in detail with reference to the diagrams. FIG. 1 shows a photoacoustic measurement system including a photoacoustic measurement apparatus according to a first embodiment of the present invention. A photoacoustic measurement system 10 has a probe (ultrasound transducer) 11, an ultrasound unit 12, and a light source 13.

The light source 13 emits measurement light. The measurement light emitted from the light source 13 is guided to the probe 11 using, for example, light guide means, such as an optical fiber, and is emitted from the probe 11 toward a subject. The light source 13 is, for example, a solid state laser light source using an yttrium aluminum garnet (YAG), alexandrite, or the like. The wavelength of measurement light is preferably a wavelength at which absorption in blood is stronger than that in the surrounding tissue, such as muscle or fat. Hereinafter, an example in which light having a wavelength of 755 nm is mainly used will be described. The type of the light source is not particularly limited, and the light source 13 may be a laser diode light source (semiconductor laser light source), or may be a light amplification type laser light source using a laser diode light source as a seed light source. Light sources other than the laser light source may be used.

The probe 11 is an acoustic wave detection unit, and has a plurality of detector elements (ultrasound transducers) arranged in a one-dimensional manner, for example. The probe 11 is not limited to the linear probe, but may be a convex probe or a sector probe. The probe 11 is disposed in a part (measurement part) for measuring the blood perfusion of the subject with echogel, water, or the like interposed therebetween. It is preferable that the probe 11 is disposed on the palm side where the amount of body hair or skin melanin is small. For example, a measurement part of the subject is placed on the stage, and the probe 11 is gripped by a grip portion provided on the stage.

At the time of measurement, a tourniquet (cuff) is wrapped at a position closer to the heart than the measurement part of the subject. It is preferable that the tourniquet includes a pump such as an air balloon for supplying air to the cuff and exhausting air from the cuff and a pressure gauge such as a mercury column for measuring the pressure applied to the cuff. More preferably, the tourniquet is capable of controlling at least one of the pressurization speed or the depressurization speed. The tourniquet is wrapped around, for example, the upper arm, and the probe 11 is placed at the center of the palm or a fingertip.

The probe 11 detects photoacoustic waves generated in the subject after measurement light is emitted to the subject in each of the avascularized condition in which the subject is avascularized and the non-avascularized condition in which the subject is not avascularized. Here, the avascularized condition refers to a state in which the blood flow in the measurement part of the subject is at least partially restricted. Preferably, the avascularized condition refers to a state in which a part closer to the heart than the measurement part of the subject is pressed with a pressure equal to or higher than the systolic blood pressure. The non-avascularized condition refers to a state in which the blood flow in the measurement part of the subject is not disturbed. Preferably, the non-avascularized condition refers to a state in which the subject is not pressed or a part closer to the heart than the measurement part of the subject is pressed with a pressure equal to or lower than the diastolic blood pressure.

The ultrasound unit 12 has a receiving circuit 21, a receiving memory 23, a photoacoustic image generation unit 25, a blood flow information generation unit 27, and a trigger control unit 28. The ultrasound unit 12 forms a photoacoustic measurement apparatus. The ultrasound unit 12 typically has a processor, a memory, a bus, and the like.

The receiving circuit 21 receives a detection signal output from the probe 11, and stores the received detection signal in the receiving memory 23. Typically, the receiving circuit 21 includes a low noise amplifier, a variable gain amplifier, a low pass filter, and an analog to digital converter (AD converter). The detection signal of the probe 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 23. The receiving circuit 21 is formed by one integral circuit (IC), for example. As the receiving memory 23, for example, a semiconductor memory is used.

The probe 11 outputs a detection signal of photoacoustic waves, and a detection signal (sampling data) of photoacoustic waves after AD conversion is stored in the receiving memory 23. The photoacoustic image generation unit 25 reads the detection signal of photoacoustic waves from the receiving memory 23, and generates a photoacoustic image based on the read detection signal of photoacoustic waves. The generation of a photoacoustic image includes, for example, image reconstruction such as phase matching addition, detection, and logarithmic conversion. For example, the photoacoustic image generation unit 25 is formed by large scale integration (LSI), such as a digital signal processor (DSP). The function of the photoacoustic image generation unit 25 may be realized by software processing using a processor included in the ultrasound unit 12.

The blood flow information generation unit 27 generates blood flow information based on the signal value of a photoacoustic image in a region of interest set in the photoacoustic image. The region of interest is set, for example, at a position away from the skin surface of the subject by a certain distance in the depth direction. The region of interest is preferably set to a region where capillaries are present. The blood flow information generation unit 27 generates blood flow information by scoring the signal value of the photoacoustic image in the region of interest. For example, a total value or an average value of the signal value of the photoacoustic image in the region of interest is calculated, and a score value based on the value is generated as blood flow information. Here, the signal value of the photoacoustic image is a value corresponding to the magnitude of the detection signal of the detected photoacoustic wave, and does not necessarily need to be the same as the pixel value of the photoacoustic image for display. Any signal in the photoacoustic image generation step can be used as the signal value of the photoacoustic image. Specifically, a detection signal of photoacoustic waves after reconstruction, a detection signal of photoacoustic waves after detection, and a detection signal of photoacoustic waves after logarithmic conversion may be used as the signal value of the photoacoustic image. The blood flow information generation unit 27 may further generate a graph showing the relationship between blood flow information and time. The blood flow information generation unit 27 is formed by a DSP, for example. The function of the blood flow information generation unit 27 may be realized by software processing using a processor included in the ultrasound unit 12.

The blood flow information generation unit 27 outputs the generated blood flow information to an image display unit 14, such as a display device. The blood flow information generation unit 27 may output a graph showing the relationship between blood flow information and time to the image display unit 14. The blood flow information generation unit 27 may display a photoacoustic image and a region of interest on the image display unit 14.

The trigger control unit 28 controls each unit in the ultrasound unit 12. For example, in the case of acquiring a photoacoustic image, the trigger control unit 28 transmits an trigger signal to the light source 13 so that measurement light is emitted from the light source 13. In addition, the trigger control unit 28 controls the sampling start timing of photoacoustic waves or the like by transmitting a sampling trigger signal to the receiving circuit 21 in response to the emission of the measurement light. The area where photoacoustic waves are to be detected may be divided into a plurality of areas. In this case, emission of light to the subject and detection of photoacoustic waves are performed for each area. For example, the trigger control unit 28 is formed by a programmable logic device (PLD), such as a field-programmable gate array (FPGA).

Measurement is performed in the following procedure. The tourniquet is wrapped around the subject, avascularization is started at a cuff pressure equal to or higher than the systolic blood pressure, for example, at a pressure of 200 mmHg, and emission of measurement light and detection of photoacoustic waves are started. After avascularization, emission of measurement light and detection of photoacoustic waves are continued while maintaining the avascularized condition. After continuing the avascularized condition for a certain period of time, the cuff pressure is rapidly reduced, for example, by releasing the valve of the air balloon. Through before and after the change in avascularized condition, the emission of measurement light and the detection of photoacoustic waves are continued. Alternatively, after continuing the avascularized condition for a certain period of time, emission of measurement light and detection of photoacoustic waves may be continued while reducing the cuff pressure stepwise at a certain rate, for example, at a rate of 2 mmHg per second. A photoacoustic image is generated based on the detection signal of photoacoustic waves detected at each time phase, and blood flow information is generated. For example, an average value of the signal value of the photoacoustic image in the region of interest is generated as blood flow information. The number of regions of interest may be one or more. In a case where there are a plurality of regions of interest, blood flow information is generated for each region of interest.

Figure 2:
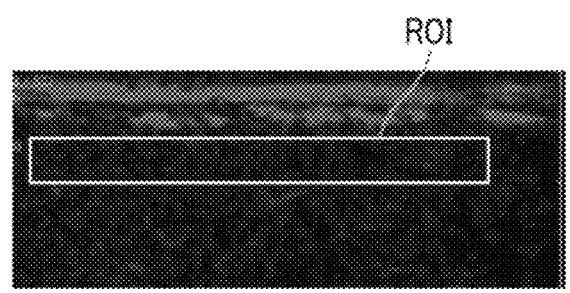
FIG. 2 is a diagram showing a photoacoustic image in an avascularized condition.

FIG. 2 shows a photoacoustic image in an avascularized condition. In FIG. 2, a region of interest ROI is set inside the subject in the depth direction. In particular, in a case where light having a wavelength of 755 nm is used as measurement light, photoacoustic waves emitted from the surface layer portion are strongly drawn in the photoacoustic image. Since a region of interest is set inside the subject in the depth direction, for example, a blood flow in a capillary or the like can be easily determined.

Figure 3:
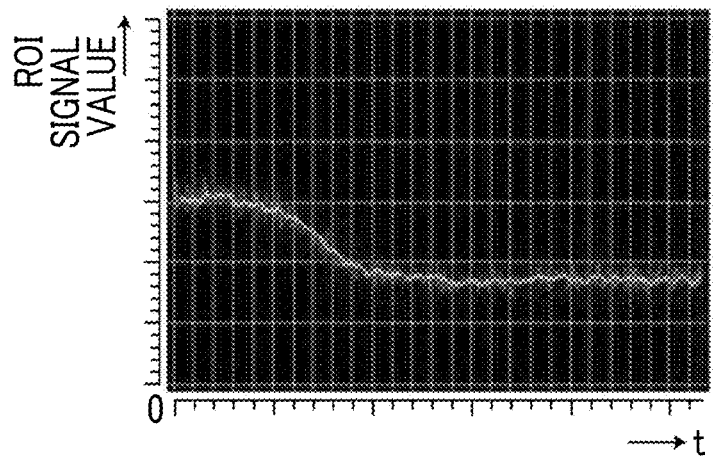
FIG. 3 is a graph showing a temporal change in the average signal value in a region of interest.

FIG. 3 is a graph showing a temporal change in the average signal value in a region of interest. A condition at time t=0 is a non-avascularized condition, and is then changed to an avascularized condition. When the non-avascularized condition is changed to the avascularized condition, a blood flow in the capillary is stopped. As a result, blood that is a light absorber is no longer present in the region of interest. Therefore, as shown in the graph of FIG. 3, the average signal value in the region of interest (ROI signal value) decreases with time and reaches a value of a certain level.

Figure 4:
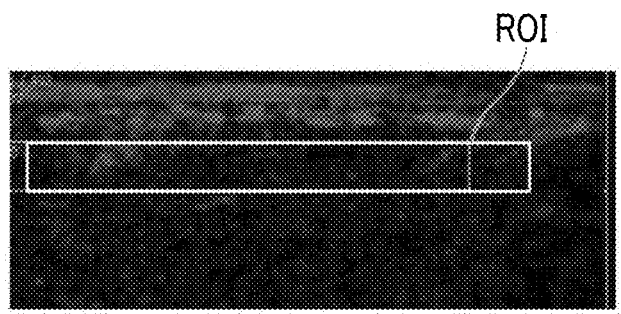
FIG. 4 is a diagram showing a photoacoustic image after a rapid change from an avascularized condition to a non-avascularized condition.

FIG. 4 shows a photoacoustic image after a rapid change from an avascularized condition to a non-avascularized condition. When the cuff pressure is rapidly reduced to cause a rapid change from the avascularized condition to the non-avascularized condition, perfusion of blood to the capillary occurs. As a result, the amount of blood present in the region of interest is increased. Therefore, the signal value (brightness) in the region of interest ROI becomes larger than that in the avascularized condition.

Figure 5:
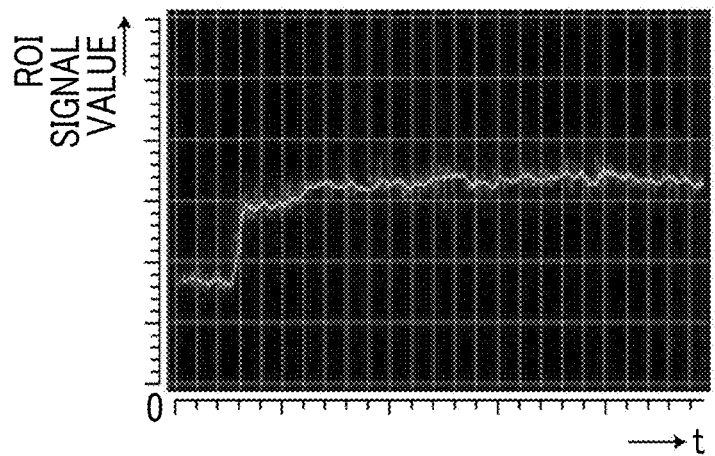
FIG. 5 is a graph showing a temporal change in the ROI signal value.

FIG. 5 is a graph showing a temporal change in the ROI signal value at the time of rapid change from an avascularized condition to a non-avascularized condition. When the avascularized condition is changed to the non-avascularized condition is made, blood stopped by avascularization starts to flow. Therefore, as shown in FIG. 5, the ROI signal value recovers to the level of a state before the avascularized condition.

Figure 6:
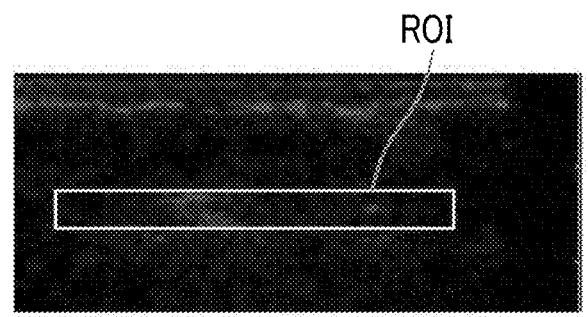
FIG. 6 is a diagram showing a photoacoustic image in a process of being changed stepwise from an avascularized condition to a non-avascularized condition.

FIG. 6 shows a photoacoustic image in a process of being changed stepwise from an avascularized condition to a non-avascularized condition. When the cuff pressure is reduced stepwise to cause a stepwise change from the avascularized condition to the non-avascularized condition, perfusion of blood to the capillary gradually occurs. As a result, the amount of blood present in the region of interest is gradually increased. Therefore, the signal value (brightness) in the region of interest ROI increases gradually from the signal value in the avascularized condition until the signal value (brightness) in the region of interest ROI reaches the level before the avascularization.

Figure 7:
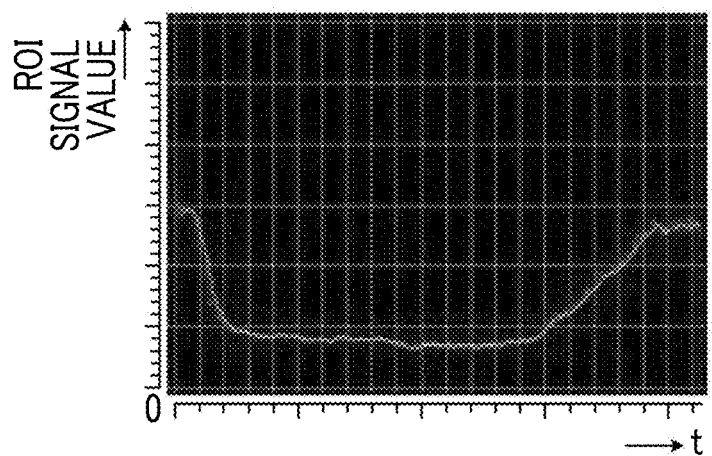
FIG. 7 is a graph showing a temporal change in the ROI signal value.

FIG. 7 is a graph showing a temporal change in the ROI signal value at the time of rapid change from an avascularized condition to a non-avascularized condition. If the cuff pressure is decreased stepwise after maintaining the avascularized condition for a certain period of time, the ROI signal value that has been reduced due to the avascularized condition increases as the cuff pressure decreases, as shown in FIG. 7. In the case of reducing the cuff pressure stepwise, the ROI signal value increases gently compared with a case of a rapid change from the avascularized condition to the non-avascularized condition (refer to FIG. 5).

Here, the intensity of a photoacoustic wave generated in the subject changes depending on the hemoglobin concentration and the oxygen saturation. In a case where light having a wavelength of 755 nm is used as the measurement light, the photoacoustic wave becomes weak as the blood volume decreases, and the photoacoustic wave becomes strong as the blood volume increases. In addition, the photoacoustic wave becomes strong as the oxygen saturation decreases, and the photoacoustic wave becomes weak as the oxygen saturation increases. When the non-avascularized condition is changed to the avascularized condition, the blood volume and the oxygen saturation are reduced. On the other hand, when the avascularized condition is changed to the non-avascularized condition, the blood volume and the oxygen saturation are increased. It is thought that the reason why the ROI signal value is reduced in the avascularized condition is that a reduction in the detection signal of the photoacoustic wave due to a reduction in blood volume is larger than an increase in the detection signal of the photoacoustic wave due to a reduction in oxygen saturation. In addition, it is thought that the reason why the ROI signal value increases at the time of non-avascularization is that an increase in the detection signal of the photoacoustic wave due to an increase in blood volume is larger than a reduction in the detection signal of the photoacoustic wave due to an increase in oxygen saturation.

Although an example in which the average value or the total value (ROI signal value) of the signal value of the photoacoustic image in the region of interest is used as blood flow information has been described above, the blood flow information is not limited thereto. The blood flow information generation unit 27 may generate, as the blood flow information, a score value based on the difference between the maximum value and the minimum value of the ROI signal value within a certain period. Alternatively, the blood flow information generation unit 27 may generate, as the blood flow information, a score value based on the difference between the ROI signal value in the avascularized condition and the ROI signal value in the non-avascularized condition.

Figure 8:
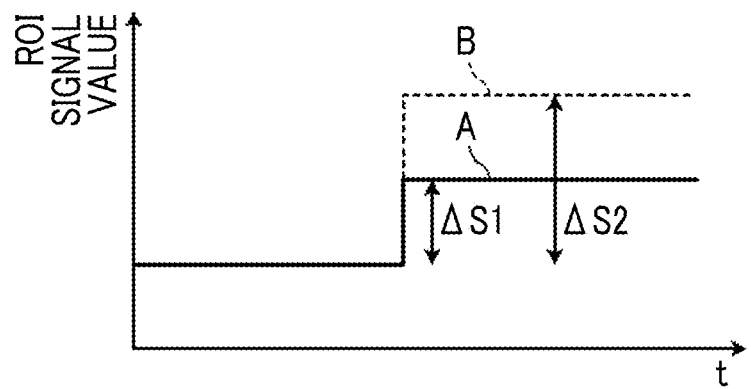
FIG. 8 is a graph showing a temporal change in the ROI signal value when an avascularized condition is changed to a non-avascularized condition.

FIG. 8 shows a graph showing a temporal change in the ROI signal value when an avascularized condition is changed to a non-avascularized condition. FIG. 8 shows a graph A showing a temporal change in the ROI signal value of a subject A and a graph B showing a temporal change in the ROI signal value of a subject B. For the subject A, the difference between the maximum and the minimum of the ROI signal value is $\Delta S1$, and $\Delta S1$ is set as the blood flow information of the subject A. For the subject B, the difference between the maximum and the minimum of the ROI signal value is $\Delta S2$, and $\Delta S2$ is set as the blood flow information of the subject B. Based on the difference between the maximum and the minimum of the ROI signal value, it is possible to evaluate how much blood is increased by perfusion compared with that at the time of avascularization. Instead of using the difference between the maximum and the minimum of the ROI signal value itself as the blood flow information, a score value obtained by converting the difference between the maximum and the minimum of the ROI signal value using a look-up table, a function, or the like may be used as the blood flow information.

Instead of the above, the blood flow information generation unit 27 may generate, as the blood flow information, a score value based on a time change rate of the ROI signal value when the avascularized condition is changed to the non-avascularized condition. The time change rate can be calculated, for example, by differentiating the ROI signal value with time.

Figure 9:
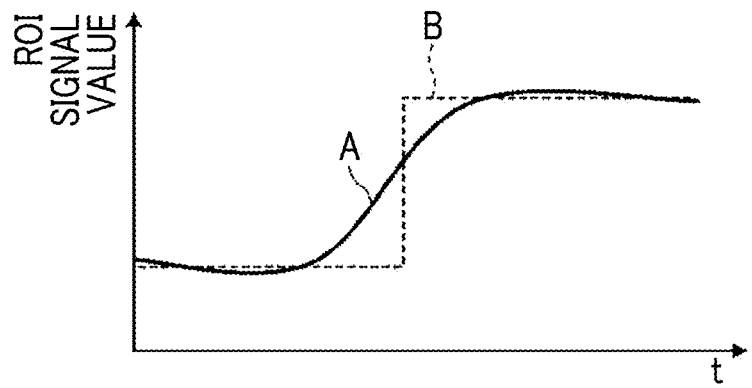
FIG. 9 is a graph showing a temporal change in the ROI signal value when an avascularized condition is changed to a non-avascularized condition.

FIG. 9 shows a graph showing a temporal change in the ROI signal value when an avascularized condition is changed to a non-avascularized condition. FIG. 9 shows a graph A showing a temporal change in the ROI signal value of the subject A and a graph B showing a temporal change in the ROI signal value of the subject B. In the case of the subject B, after a change to the non-avascularized condition, the ROI signal value recovers to the level before the avascularization earlier than in the case of the subject A. Therefore, the time change rate (the maximum value) of the ROI signal value of the subject B is larger than that of the subject A. Based on the magnitude of the time change rate, it is possible to evaluate the blood increase rate due to perfusion.

The blood flow information generation unit 27 may generate, as the blood flow information, a score value based on the time from the reference time to the time, at which the ROI signal value reaches a certain level, when the avascularized condition is changed to the non-avascularized condition. The reference time may be, for example, a time at which the avascularized condition is changed to the non-avascularized condition. Alternatively, in a case where the cuff pressure is changed stepwise, a time at which the cuff pressure starts to change may be set as the reference time.

Figure 10:
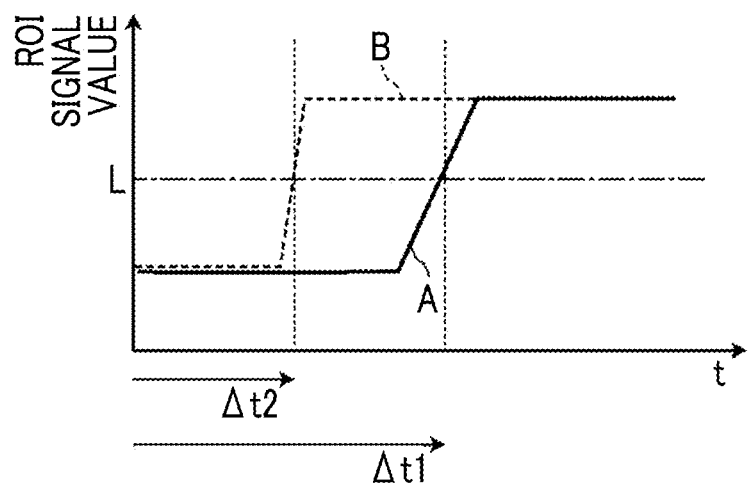
FIG. 10 is a graph showing a temporal change in the ROI signal value when an avascularized condition is changed to a non-avascularized condition.

FIG. 10 shows a graph showing a temporal change in the ROI signal value when an avascularized condition is changed to a non-avascularized condition. FIG. 10 shows a graph A showing a temporal change in the ROI signal value of the subject A and a graph B showing a temporal change in the ROI signal value of the subject B. In the case of the subject B, after a change to the non-avascularized condition, the ROI signal value reaches a certain level L earlier than in the case of the subject A. The ROI signal value of the subject A reaches the certain level L after $\Delta t1$ from the reference time. On the other hand, the subject B reaches the certain level L after $\Delta t2$ ($<\Delta t1$) from the reference time. Based on the time to reach the certain level L, it is possible to evaluate the blood increase rate due to perfusion.

In addition, the blood flow information generation unit 27 may generate, as the blood flow information, a score value based on the ROI signal value at a time when a certain time has passed from the reference time when the avascularized condition is changed to the non-avascularized condition. As described above, the reference time may be, for example, a time at which the avascularized condition is changed to the non-avascularized condition. Alternatively, in a case where the cuff pressure is changed stepwise, a time at which the cuff pressure starts to change may be set as the reference time.

Figure 11:
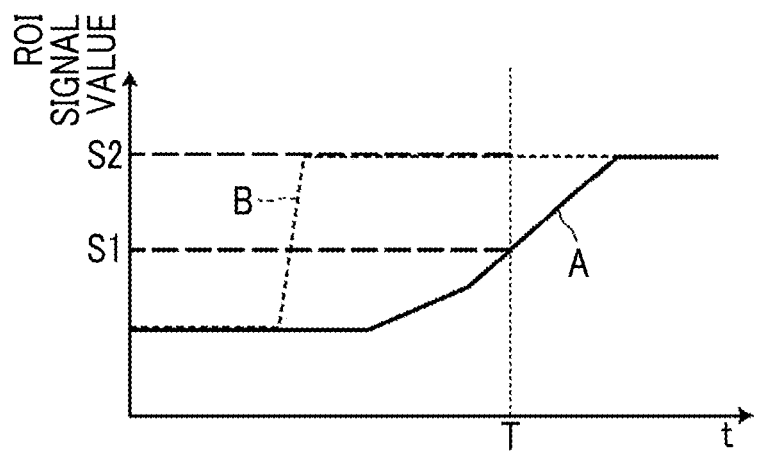
FIG. 11 is a graph showing a temporal change in the ROI signal value when an avascularized condition is changed to a non-avascularized condition.

FIG. 11 shows a graph showing a temporal change in the ROI signal value when an avascularized condition is changed to a non-avascularized condition. FIG. 11 shows a graph A showing a temporal change in the ROI signal value of the subject A and a graph B showing a temporal change in the ROI signal value of the subject B. The ROI signal value of the subject B already reaches a level S2 before the avascularized condition at the time T when a certain time has passed from the reference time. On the other hand, at the time T, the ROI signal value of the subject A is S1 (<S2) since the ROI signal value of the subject A does not reach the level before the avascularized condition. Based on the ROI signal value at the time T, it is possible to evaluate the blood increase rate due to perfusion.

Here, since the ROI signal value depends on the signal value of the detection signal of the photoacoustic wave, the ROI signal value is strongly influenced by a relatively thick blood vessel having a large blood flow (having a large signal value) or the like. In order to evaluate the blood perfusion state of a fine blood vessel for nourishing the tissue, it is preferable to perform evaluation using an amount that does not depend on the signal intensity, for example, a binary amount. It is preferable that binarization is performed so as to distinguish between a range from a lower threshold value to an upper threshold value and the outside of the range. For example, the blood flow information generation unit 27 may binarize the signal value of the photoacoustic image by setting the signal value of the photoacoustic image to a first value (for example, a signal value 1) when the signal value of the photoacoustic image is equal to or greater than a first threshold value (corresponding to a lower threshold value) and equal to or less than a second threshold value (corresponding to an upper threshold value) larger than the first threshold value and setting the signal value of the photoacoustic image to a second value (for example, a signal value 0) when the signal value of the photoacoustic image is less than the first threshold value or greater than the second threshold value, and generate the blood flow information based on the binarized signal value of the photoacoustic image. More specifically, the blood flow information generation unit 27 may add binarized values in a region of interest and generate a value standardized by the area of the region of interest as the blood flow information.

In the present embodiment, a photoacoustic image is generated by performing light emission and photoacoustic wave detection in each of the avascularized condition and the non-avascularized condition, and blood flow information is generated based on the signal value of the photoacoustic image in the region of interest. In this manner, it is possible to generate blood flow information in a desired region using a photoacoustic image. In particular, by setting a region of interest inside the subject in the depth direction, it is possible to generate blood flow information for evaluating the perfusion in a deep part or a fine blood vessel without being influenced by artifacts on the subject surface or the like.

Although an example in which light having a wavelength of 755 nm is mainly used as the measurement light has been described above, the wavelength of the measurement light is not limited thereto. For example, light having a wavelength of 1064 nm or 800 nm may be used as the measurement light.

The number of wavelengths of the measurement light is not limited to one, and measurement light having a plurality of wavelengths may be used. As described above, the value of the photoacoustic wave generated in the subject changes depending on the hemoglobin concentration and the oxygen saturation, and the manner of the change varies depending on the wavelength of the measurement light. For example, in a case where the wavelength of the measurement light is 755 nm, a more intense photoacoustic wave is generated from a vein having lower oxygen saturation between the artery and the vein. In a case where the wavelength of the measurement light is 1064 nm, a more intense photoacoustic wave is generated from the artery having higher oxygen saturation. In other words, in a case where the wavelength of the measurement light is 755 nm, the detection signal of the photoacoustic wave increases when the oxygen saturation is low. In a case where the wavelength of the measurement light is 1064 nm, the detection signal of the photoacoustic wave increases when the oxygen saturation is high. In a case where the wavelength of the measurement light is 800 nm, the intensity of the generated photoacoustic wave hardly changes with the oxygen saturation. By detecting a photoacoustic wave using light having a wavelength of 755 nm and light having a wavelength of 1064 nm as the measurement light and examining the wavelength dependence of the detection signal of the photoacoustic wave, the blood flow and the oxygen saturation can be separated. The combination of wavelengths is not limited to those described above. For example, light having a wavelength of 755 nm and light having a wavelength of 800 nm may be used as the measurement light. Thus, since the blood flow and the oxygen saturation can be separated by using the measurement light having a plurality of wavelengths, the blood flow information generation unit 27 can generate blood flow information relevant to the oxygen saturation instead of or in addition to the blood flow information relevant to the blood flow.

Figure 12:
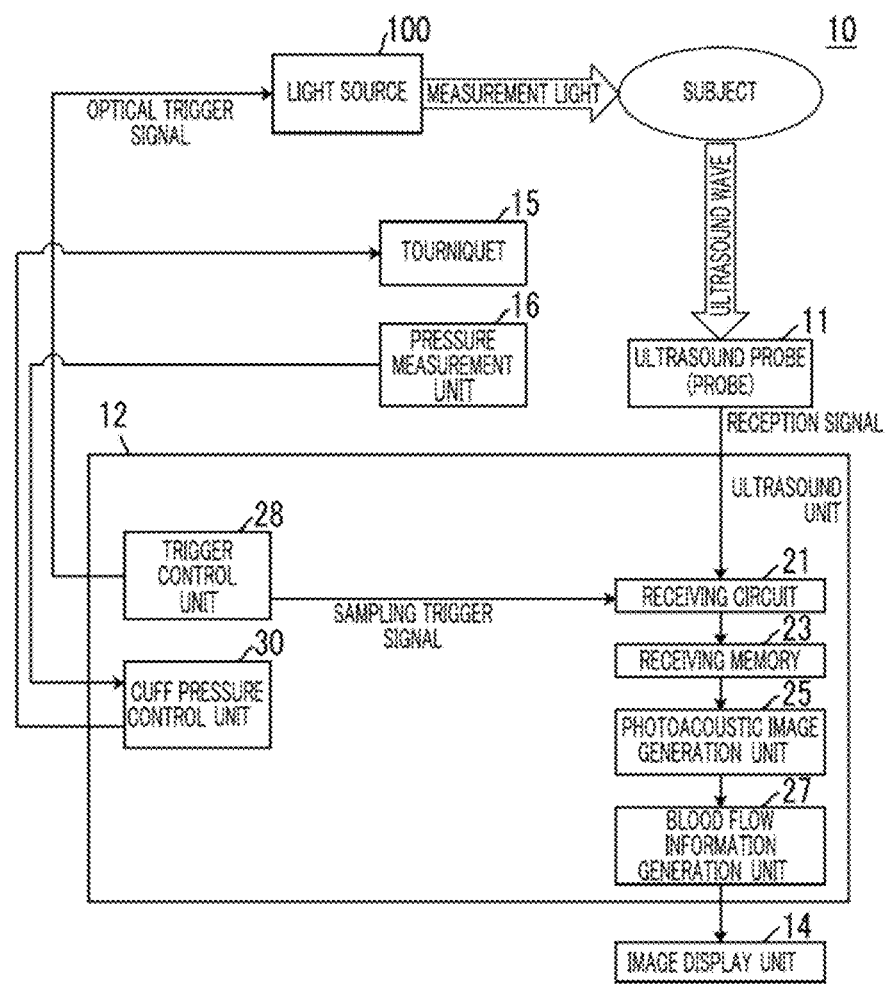
FIG. 12 is a block diagram showing a photoacoustic measurement system according to a second embodiment of the present invention.

Next, a second embodiment of the present invention will be described. FIG. 12 shows a photoacoustic measurement system according to the second embodiment of the present invention. A photoacoustic measurement system 10 of the present embodiment further has a tourniquet 15 and a pressure measurement unit 16 in addition to the components of the photoacoustic measurement system 10 according to the first embodiment shown in FIG. 1. In addition, the ultrasound unit 12 further has a cuff pressure control unit 30.

The tourniquet 15 is a tourniquet with a variable cuff pressure. It is possible to increase the cuff pressure by supplying air to the tourniquet 15 using a pump or the like attached to the tourniquet 15 and to reduce the cuff pressure by opening the exhaust valve. The pressure measurement unit 16 is, for example, a pressure sensor, and measures the cuff pressure of the tourniquet 15. The cuff pressure control unit 30 controls the cuff pressure of the tourniquet 15. The cuff pressure control unit 30 controls the cuff pressure of the tourniquet 15 to a desired pressure based on the cuff pressure measured by the pressure measurement unit 16. For the cuff pressure control unit 30, for example, an FPGA is used.

When the measurement is started, the cuff pressure control unit 30 increases the cuff pressure of the tourniquet 15 so that the subject is in the avascularized condition. Then, after maintaining the avascularized condition for a certain period of time, the cuff pressure is reduced stepwise so that the subject is in the non-avascularized condition. In the meantime, emission of measurement light to the subject and detection of photoacoustic waves are continued. The blood flow information generation unit 27 generates blood flow information based on the photoacoustic image, and stores the blood flow information so as to be associated with the cuff pressure. In the present embodiment, the blood flow information generation unit 27 may further generate a graph showing the relationship between the blood flow information and the cuff pressure.

Figure 13:
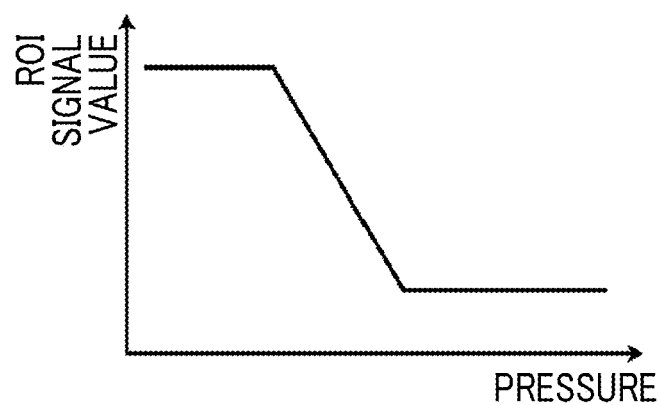
FIG. 13 is a graph showing the relationship between the ROI signal value and the cuff pressure.

FIG. 13 is a graph showing the relationship between the ROI signal value and the cuff pressure. When the ROI signal value is plotted with respect to the cuff pressure, the graph shown in FIG. 13 is obtained. By referring to this graph, it is possible to know the cuff pressure at which perfusion of blood starts, the inclination of the ROI signal value with respect to the cuff pressure, the cuff pressure at which the blood flow reaches a level before the avascularized condition, and the like. Therefore, it is possible to evaluate the perfusion of the subject.

In the present embodiment, emission of light to the subject and measurement of a photoacoustic wave are performed while measuring the cuff pressure. By associating the cuff pressure with the blood flow information generated based on the photoacoustic image, it is possible to generate a graph showing the relationship between the blood flow information and the cuff pressure. By referring to such a graph, it is possible to evaluate perfusion. In addition, in the present embodiment, since the cuff pressure control unit 30 performs the avascularization of the subject, there is also the merit that the measurement can be at least partially automated.

Subsequently, a third embodiment of the present invention will be described. The configuration of a photoacoustic measurement system according to the third embodiment of the present invention is the same as the configuration of the photoacoustic measurement system 10 according to the first embodiment shown in FIG. 1. Alternatively, the configuration of the photoacoustic measurement system according to the third embodiment of the present invention may be the same as the configuration of the photoacoustic measurement system 10 according to the second embodiment shown in FIG. 12. In the present embodiment, the blood flow information generation unit 27 further generates a blood flow information image based on the blood flow information. Others are the same as those in the first embodiment or the second embodiment.

In the present embodiment, a plurality of regions of interest are set in a photoacoustic image. For example, in a photoacoustic image, a plurality of regions of interest are set in a grid form in a region indicating an outer frame. The blood flow information generation unit 27 generates blood flow information for each of the plurality of regions of interest. The blood flow information image generated by the blood flow information generation unit 27 is a space map image for displaying the blood flow information of each region of interest in the region of interest. In the blood flow information image, each region of interest is displayed with a brightness corresponding to the blood flow information.

Figure 14:
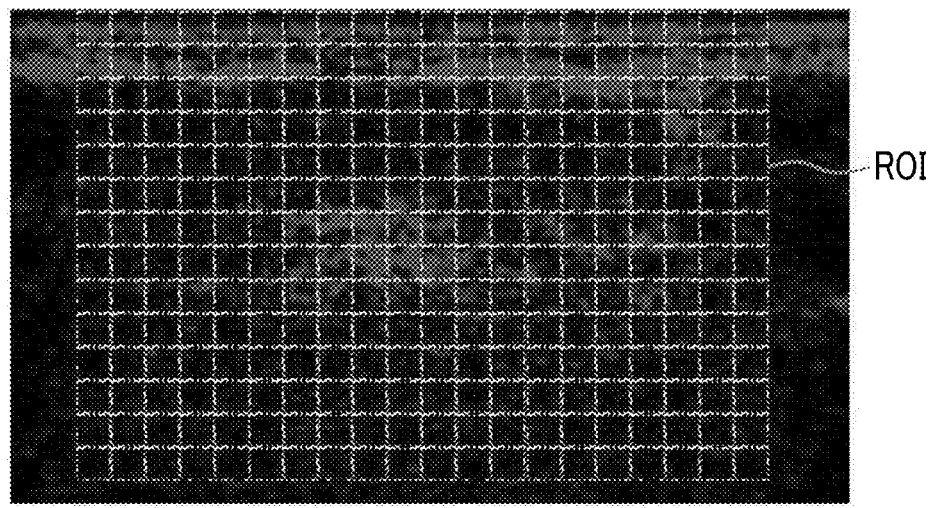
FIG. 14 is a diagram showing a plurality of regions of interest set in a grid form in a photoacoustic image.

FIG. 14 shows a plurality of regions of interest set in a grid form in a photoacoustic image. In the photoacoustic image, the regions of interest ROI are set in a grid form in a region indicating an outer frame. Since the regions of interest ROI are set in a grid form as described above, it is possible to evaluate the perfusion state of blood in the width direction and the depth direction of the image.

The blood flow information generation unit 27 generates, for example, a difference between the maximum value and the minimum value of the ROI signal value within a certain period, as blood flow information, for each of the regions of interest ROI in a grid form. For example, the ROI signal value is calculated by calculating the total value of the signal value of the photoacoustic image in the region of interest ROI and standardizing the total value with the area of the region of interest ROI. When calculating the total value of the signal value of the photoacoustic image in the region of interest ROI, the signal value of the photoacoustic image may be binarized.

Figure 15:
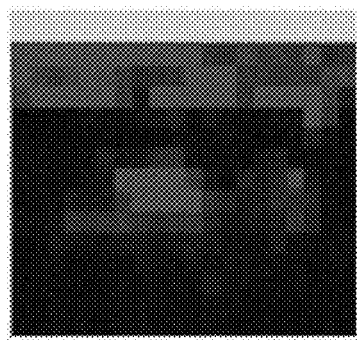
FIG. 15 is a diagram showing an image example of a blood flow information image.

FIG. 15 shows an image example of a blood flow information image. In the blood flow image, the brightness of each pixel corresponds to the magnitude of the blood flow information on each region of interest ROI (refer to FIG. 14). By referring to the blood flow image shown in FIG. 15, it is possible to evaluate the amount of perfusion of blood in each part in the subject.

The blood flow information generation unit 27 generates a blood flow information image in time series, for example. In this case, the blood flow information generation unit 27 may set the display color of each region of interest in the blood flow information image to a different display color in a case where blood flow information at the first time is larger than blood flow information at the second time earlier than the first time and a case where the blood flow information at the first time is smaller than the blood flow information at the second time. One example of the first time is, for example, a current time. As a more specific example, the first time is a (current) time at which the blood flow information image is displayed on the screen. However, the first time is not limited thereto. For example, red may be set as a display color for a part where the blood flow is increasing and the blood flow information at the first time is larger than the blood flow information at the second time, and blue may be set as a display color for a part where the blood flow is decreasing and the blood flow information at the first time is smaller than the blood flow information at the second time. In this case, by referring to the blood flow image, it becomes easy to understand in which part the blood has increased and in which part the blood has decreased.

In the present embodiment, a blood flow information image is generated based on blood flow information. By imaging the blood flow information, it becomes easy to grasp the spatial distribution of blood flow information. In particular, in the case of comparing a plurality of regions of interest ROI, it becomes easy to compare the local behaviors of the overall behavior by map-displaying the blood flow information of the region of interest ROI corresponding to the position of the region of interest ROI of the photoacoustic image. Other effects are the same as those of the first embodiment or the second embodiment.

Figure 16:
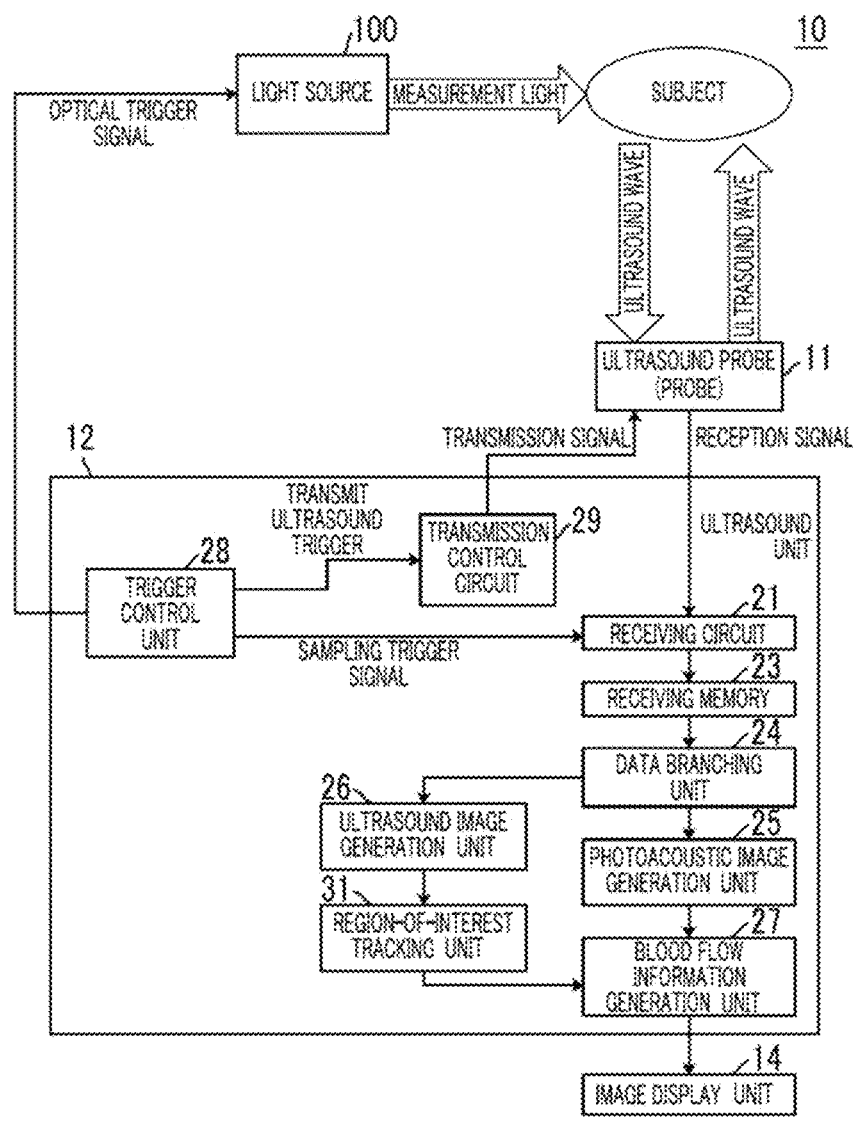
FIG. 16 is a block diagram showing a photoacoustic measurement system according to a fourth embodiment of the present invention.

Subsequently, a fourth embodiment of the present invention will be described. FIG. 16 shows a photoacoustic measurement system according to the fourth embodiment of the present invention. A photoacoustic measurement system 10 of the present embodiment is different from the photoacoustic measurement system 10 of the first embodiment shown in FIG. 1 in that the ultrasound unit 12 further has a data branching unit 24, an ultrasound image generation unit 26, a transmission control circuit 29, and a region-of-interest tracking unit 31. Others may be the same as those in the first to third embodiments. In the embodiment of the present invention, an ultrasound wave is used as an acoustic wave. However, the acoustic wave is not limited to the ultrasound wave, and an acoustic wave having an audible frequency may be used as long as an appropriate frequency can be selected according to an examination target, measurement conditions, or the like.

In the present embodiment, in addition to the detection of photoacoustic waves, the probe 11 performs transmission of acoustic waves (ultrasound waves) to the subject and reception of reflected acoustic waves (reflected ultrasound waves) of the transmitted ultrasound waves. Transmission and reception of ultrasound waves may be performed at separate positions. For example, ultrasound waves may be transmitted from a position different from the probe 11, and reflected ultrasound waves of the transmitted ultrasound waves may be received by the probe 11.

The probe 11 outputs a detection signal of photoacoustic waves and a detection signal of reflected ultrasound waves, and detection signals (sampling data) of photoacoustic waves and reflected ultrasound waves after AD conversion are stored in the receiving memory 23. The data branching unit 24 is, for example, a changeover switch, and transmits the sampling data of the detection signal of photoacoustic waves read from the receiving memory 23 to the photoacoustic image generation unit 25. The data branching unit 24 transmits the sampling data of the reflected ultrasound waves read from the receiving memory 23 to the ultrasound image generation unit 26. The ultrasound image generation unit (reflected acoustic wave image generation unit) 26 generates an ultrasound image (reflected acoustic wave image) based on the detection signal of reflected ultrasound waves detected by the probe 11. For the ultrasound image generation unit 26, for example, a DSP is used. The function of the ultrasound image generation unit 26 may be realized by software processing using a processor included in the ultrasound unit 12. The generation of an ultrasound image also includes image reconstruction such as phase matching addition, detection, and logarithmic conversion. The generated ultrasound image may be displayed on the image display unit 14.

In the case of acquiring an ultrasound image, the trigger control unit 28 transmits an ultrasound wave transmission trigger signal for giving an instruction to transmit ultrasound waves to the transmission control circuit 29. When the ultrasound wave transmission trigger signal is received, the transmission control circuit 29 makes the probe 11 transmit ultrasound waves. For the transmission control circuit 29, for example, an FPGA is used. The probe 11 detects reflected ultrasound waves by performing a scan while shifting the acoustic line by one line at a time, for example. The trigger control unit 28 transmits a sampling trigger signal to the receiving circuit 21 according to the timing of ultrasound wave transmission, thereby starting the sampling of reflected ultrasound waves. Acquisition of a photoacoustic image and acquisition of an ultrasound image may be performed in synchronization with each other.

Here, since the position of the subject changes due to body motion or the like, the position of the region of interest of the photoacoustic image may change between frames. An ultrasound image is used for correction of positional deviation between frames. The region-of-interest tracking unit 31 tracks the position of the region of interest using the ultrasound image. In particular, the region-of-interest tracking unit 31 tracks the position of the region of interest using a plurality of consecutive ultrasound images (a plurality of consecutive frames). The region-of-interest tracking unit 31 detects motion of an image between frames using a method, such as template matching between frames, for example. For the region-of-interest tracking unit 31, for example, a DSP is used. The function of the region-of-interest tracking unit 31 may be realized by software processing using a processor included in the ultrasound unit 12. The region-of-interest tracking unit 31 moves the position of the region of interest by the amount of detected motion of the image between the frames, and notifies the blood flow information generation unit 27 of the moved position of the region of interest. The blood flow information generation unit 27 generates blood flow information using the notified position of the region of interest. In generating blood flow information, it is preferable that the region of interest does not include a region outside the body. It is preferable to detect a skin boundary in a region of interest in the ultrasound image generated in synchronization with the photoacoustic image and set a part in a direction of the inside of the subject rather than the skin boundary as the area of the region of interest.

In the present embodiment, the ultrasound image generation unit 26 generates an ultrasound image. By using the ultrasound image, it is possible to detect the motion of the image between the frames and track the region of interest between the frames. In this case, even when a positional deviation occurs due to body motion or the like, it is possible to generate the blood flow information of the same part in the subject. Therefore, it is possible to improve the accuracy of the generated blood flow information. Other effects are the same as those of the first to third embodiments.

While the present invention has been described based on the preferred embodiments, the photoacoustic measurement apparatus and the photoacoustic measurement system of the present invention are not limited to the above embodiments, and various modifications and changes in the configurations of the above embodiments are also included in the range of the present invention.

EXPLANATION OF REFERENCES

10: photoacoustic measurement system
11: probe
12: ultrasound unit
13: light source
14: image display unit
15: tourniquet
16: pressure measurement unit
21: receiving circuit
23: receiving memory
24: data branching unit
25: photoacoustic image generation unit
26: ultrasound image generation unit
27: blood flow information generation unit
28: trigger control unit
29: transmission control circuit
30: cuff pressure control unit
31: region-of-interest tracking unit

What is claimed is:

1. A photoacoustic measurement apparatus, comprising:
a receiving circuit that receives a detection signal of a photoacoustic wave, which is generated in a subject due to emission of measurement light to the subject, in each of at least an avascularized condition in which the subject is avascularized and a non-avascularized condition in which the subject is not avascularized;
a processor configured to
generate a photoacoustic image for each of the avascularized condition and the non-avascularized condition based on the detection signal of the photoacoustic wave; and
generate blood flow information based on a signal value of each of the photoacoustic images in a region of interest set in the photoacoustic images,
wherein the processor is configured to calculate a total value or an average value of the signal value in the region of interest for each time point or time frame, the each time point or the time frame corresponding to one of the photoacoustic images, and
wherein the processor further generates, as the blood flow information, a score value based on a difference between the total value or the average value of the signal value in the region of interest in the avascularized condition and the total value or the average value of the signal value in the region of interest in the non-avascularized condition.

2. The photoacoustic measurement apparatus according to claim 1, further comprising:
a tourniquet capable of changing a cuff pressure in order to bring the subject into the avascularized condition and the non-avascularized condition.

3. The photoacoustic measurement apparatus according to claim 2, the processor further configured to:
control a cuff pressure of the tourniquet.

4. The photoacoustic measurement apparatus according to claim 1,
wherein the processor binarizes the signal value by setting the signal value to a first value when the signal value is equal to or greater than a first threshold value and equal to or less than a second threshold value larger than the first threshold value and setting the signal value to a second value different from the first value when the signal value is less than the first threshold value or greater than the second threshold value, and generates the blood flow information based on the binarized signal value.

5. The photoacoustic measurement apparatus according to claim 2,
wherein the processor binarizes the signal value by setting the signal value to a first value when the signal value is equal to or greater than a first threshold value and equal to or less than a second threshold value larger than the first threshold value and setting the signal value to a second value different from the first value when the signal value is less than the first threshold value or greater than the second threshold value, and generates the blood flow information based on the binarized signal value.

6. The photoacoustic measurement apparatus according to claim 1,
wherein the processor further generates a graph showing a relationship between the blood flow information and time.

7. The photoacoustic measurement apparatus according to claim 1,
wherein the receiving circuit further receives a detection signal of a reflected acoustic wave with respect to an acoustic wave transmitted to the subject,
the processor further configured to
generate a reflected acoustic wave image based on the detection signal of the reflected acoustic wave; and
track a position of the region of interest using the reflected acoustic wave image.

8. The photoacoustic measurement apparatus according to claim 1,
wherein the processor generates, as blood flow information, a total value or an average value of the signal value in the region of interest.

9. The photoacoustic measurement apparatus according to claim 1, further comprising:
a pressure measurement sensor configured to measure a cuff pressure of the subject,
wherein the processor further generates a graph showing a relationship between the blood flow information and the avascularization pressure.

10. The photoacoustic measurement apparatus according to claim 1,
wherein the processor calculates a total value or an average value of the signal value in the region of interest in a certain period, and generates, as the blood flow information, a score value based on a difference between a minimum value and a maximum value of the total value or the average value in the certain period, repeatedly.

11. The photoacoustic measurement apparatus according to claim 1,
wherein the processor is configured to calculate a total value or an average value of the signal value in the region of interest for each time point or time frame,
wherein, in a case where the subject is changed from the avascularized condition to the non-avascularized condition, the processor further generates, as the blood flow information, a score value based on a time change rate of the total value or the average value of the signal value in the region of interest.

12. The photoacoustic measurement apparatus according to claim 1,
wherein the processor is configured to calculate a total value or an average value of the signal value in the region of interest for each time point or time frame,
wherein, in a case where the subject is changed from the avascularized condition to the non-avascularized condition, the processor further generates, as the blood flow information, a score value based on the total value or the average value of the signal value in the region of interest after a certain time has passed from a reference time.

13. The photoacoustic measurement apparatus according to claim 1,
wherein the processor is configured to calculate a total value or an average value of the signal value in the region of interest for each time point or time frame,
wherein, in a case where the subject is changed from the avascularized condition to the non-avascularized condition, the processor further generates, as the blood flow information, a score value based on a time from a reference time to a time at which the total value or the average value of the signal value in the region of interest reaches a certain level.

14. The photoacoustic measurement apparatus according to claim 1,
wherein the processor further generates a blood flow information image based on the blood flow information.

15. The photoacoustic measurement apparatus according to claim 14,
wherein, in a case where a plurality of the regions of interest are set, the blood flow information is generated for each of the plurality of regions of interest, and the blood flow information image is a space map image for displaying blood flow information of each region of interest in the region of interest.

16. The photoacoustic measurement apparatus according to claim 15,
wherein, in the blood flow information image, each region of interest is displayed with a brightness corresponding to the blood flow information.

17. The photoacoustic measurement apparatus according to claim 15,
wherein the processor sets a display color of each region of interest in the blood flow information image to a different display color in a case where blood flow information at a first time is larger than blood flow information at a second time earlier than the first time and a case where the blood flow information at the first time is smaller than the blood flow information at the second time.

18. The photoacoustic measurement apparatus according to claim 1,
wherein a plurality of the regions of interest are set in a grid form.

19. A photoacoustic measurement system, comprising:
a light source that emits measurement light; and
the photoacoustic measurement apparatus according to claim 1.

20. A photoacoustic measurement apparatus, comprising:
a receiving circuit that receives a detection signal of a photoacoustic wave, which is generated in a subject due to emission of measurement light to the subject, in each of at least an avascularized condition in which the subject is avascularized and a non-avascularized condition in which the subject is not avascularized;
a processor configured to
generate a photoacoustic image for each of the avascularized condition and the non-avascularized condition based on the detection signal of the photoacoustic wave; and
generate blood flow information based on a signal value of each of the photoacoustic images in a region of interest set in the photoacoustic images,
wherein the processor repeatedly calculates a total value or an average value of the signal value in the region of interest in a certain period, the certain period corresponding to one of the photoacoustic images and generates, as the blood flow information, a score value based on a difference between a minimum value and a maximum value of the total values or the average values in the certain period.

* * * * *